(12) United States Patent
Asia et al.

(10) Patent No.: US 7,135,016 B1
(45) Date of Patent: Nov. 14, 2006

(54) NON-PENETRATING FILTRATION SURGERY

(75) Inventors: Ehud Asia, Tel-Aviv (IL); Alex Harel, Savyon (IL); Adi Shargil, Bnei-Zion (IL)

(73) Assignee: Optotech Ltd., Nazereth-Ilit (IL)

( * ) Notice: Subject to any disclaimer, the term of this patent is extended or adjusted under 35 U.S.C. 154(b) by 0 days.

(21) Appl. No.: 10/240,505

(22) PCT Filed: May 8, 2000

(86) PCT No.: PCT/IL00/00263

§ 371 (c)(1),
(2), (4) Date: Sep. 30, 2002

(87) PCT Pub. No.: WO01/85044

PCT Pub. Date: Nov. 15, 2001

(51) Int. Cl.
*A61B 18/18* (2006.01)

(52) U.S. Cl. .................. 606/5; 606/4; 606/6; 606/12

(58) Field of Classification Search ............. 606/4–6, 606/10–12, 17, 18; 607/88, 89, 91; 128/898
See application file for complete search history.

(56) References Cited

U.S. PATENT DOCUMENTS

| | | | | |
|---|---|---|---|---|
| 4,665,913 A | * | 5/1987 | L'Esperance, Jr. | 606/3 |
| 4,907,586 A | | 3/1990 | Bille et al. | |
| 4,963,142 A | | 10/1990 | Loertscher | |
| 5,098,426 A | | 3/1992 | Sklar et al. | |
| 5,364,390 A | * | 11/1994 | Taboada et al. | 606/10 |
| 5,370,641 A | * | 12/1994 | O'Donnell, Jr. | 606/4 |
| 5,520,679 A | | 5/1996 | Lin | |
| 5,529,076 A | * | 6/1996 | Schachar | 128/898 |
| 5,620,435 A | | 4/1997 | Belkin et al. | |
| 5,634,920 A | | 6/1997 | Hohla | |
| 5,733,276 A | | 3/1998 | Belkin | |
| 5,738,677 A | | 4/1998 | Colvard et al. | |
| 5,782,822 A | * | 7/1998 | Telfair et al. | 606/5 |
| 5,827,266 A | | 10/1998 | Harel et al. | |
| 6,010,497 A | | 1/2000 | Tang et al. | |
| 6,059,772 A | * | 5/2000 | Hsia et al. | 606/4 |
| 6,159,202 A | | 12/2000 | Sumiya et al. | |
| 6,220,247 B1 | | 4/2001 | Maldonado Bas | |
| 6,241,721 B1 | | 6/2001 | Cozean et al. | |

(Continued)

FOREIGN PATENT DOCUMENTS

EP    0 765 648    4/1997

(Continued)

OTHER PUBLICATIONS

Barak, A. et al; "Anterior Capsulotomy Using CO2 Laser;" SPIE; vol. 3246; pp. 196-198; Jun. 1998.

(Continued)

*Primary Examiner*—A. Farah
(74) *Attorney, Agent, or Firm*—Fenster & Company (57) ABSTRACT

This invention is an apparatus for ophthalmic surgery comprising a laser source (52) that generates a laser beam (54); a scanner (56) comprising an input for said laser beam, and an output of a spatially scanned laser beam (54); controlling circuitry that drives said scanner (56) to remove tissue in a desired pattern on the eye (40); a microscope (58) for viewing said tissue removal; and a beam combiner (70) comprising a first input for a line of sight of said microscope (58) and second input for said spatially scanned beam (54).

28 Claims, 5 Drawing Sheets

U.S. PATENT DOCUMENTS

| | | |
|---|---|---|
| 6,258,082 B1 | 7/2001 | Lin |
| 6,263,879 B1 * | 7/2001 | Lin .......................... 128/898 |
| 6,540,391 B1 * | 4/2003 | Lanzetta et al. ............ 362/553 |
| 2001/0029363 A1 | 10/2001 | Lin |
| 2002/0026179 A1 | 2/2002 | Toh |

FOREIGN PATENT DOCUMENTS

| | | |
|---|---|---|
| EP | 0 770 370 | 5/1997 |
| EP | 1 138 290 | 10/2001 |
| WO | WO 01/50969 | 7/2001 |

OTHER PUBLICATIONS

Assia, E. I. et al.; "Non-Penetrating Glaucoma Surgery Using the $CO_2$ Laser: Experimental Studies in Human Cadaver Eyes;" Proceedings of SPIE; vol. 4245; pp. 228-233; Jun. 2001.

Belkin, M. et al.; "Non-Penetrating Trabeculectomy Using the $CO_2$ Laser in Rabbits;" Abstract No. 1419-B327; IOVS; vol. 40; No. 4; Mar. 15, 1999.

Wolbarsht, M.; "Laser Surgery: $CO_2$ or HF;" IEEE Journal of Quantum Electronics; vol. QE-20; No. 12; pp. 1427-1432; Dec. 1984.

* cited by examiner

FIG. 8B

NON-PENETRATING FILTRATION SURGERY

RELATED APPLICATIONS

This application is a U.S. national filing of PCT Application No. PCT/IL00/00263 filed May 8, 2000.

FIELD OF THE INVENTION

The present invention is related to the field of Glaucoma treatment using laser ablation.

BACKGROUND OF THE INVENTION

Glaucoma is an optical neuropathy associated with increased intraocular pressure. The mechanism of the disease is not fully understood. However, the most effective therapy appears to be reducing the intraocular pressure, for example using medication or implants. Further damage to the optic nerve is thus prevented or reduced.

One procedure that has been suggested is non-penetrating trabeculectomy, in which a portion of the sclera overlying the Schlemm's canal is removed, allowing aqueous humor to leave the eye. It is desirable to remove only part of the thickness of the sclera, preventing penetration into the eye. However, this procedure is difficult to perform with a knife.

U.S. Pat. No. 5,370,641 to O'Donnell, the disclosure of which is incorporated herein by reference, describes using an excimer laser to ablate the sclera overlying the Schlemm's canal and the trabecular meshwork. The laser spot size and treatment area are not described. This patent states that when a sufficient amount of the corneoscleral bed is removed, aqueous humor comes through the remaining ultra-thin Schlemm's canal and trabecular meshwork and the energy of the laser is absorbed by the out-flowing humor, creating a self-regulating end point.

However, even though many years have passed since this patent was issued, the method taught in the patent has not found wide-spread use, in spite of a great need in the art of treating Glaucoma, a disease for which there is no completely satisfactory treatment.

SUMMARY OF THE INVENTION

An aspect of some embodiments of the invention relates to apparatus for effecting and controlling a non-penetrating filtration procedure. In an exemplary embodiment of the invention, the apparatus includes a scanner for automatically scanning an area of the eye using a laser spot, thereby ablating over the entire area. Optionally, a continuous scan is used, with the laser beam on at all times. A potential advantage of using a scanner is the ability to provide a large total amount of energy to a large area of the eye using a relatively inexpensive laser and scanning the beam over the area.

In an embodiment of the invention, an area of scleral and/or corneal tissue is ablated or otherwise removed by a laser. When sufficient scleral tissue is ablated by the laser, there is a percolation of aqueous humor. Optionally, this humor absorbs the laser energy and prevents or significantly slows further penetration, even for significant laser energy levels. Alternatively or additionally, the aqueous humor assists in dispersing the heat generated by the laser. Optionally, a $CO_2$ laser is used.

Another potential advantage of using a scanner is that a uniform percolation profile (or another desired profile) can be achieved. Optionally, a uniform final tissue thickness is created by the ablation. Alternatively, different tissue types or areas may have different thickness, so that a uniform percolation is achieved. In some cases, the ablated sclera or cornea thickness will vary responsive to the underlying tissue.

In some embodiments of the invention, a reservoir is ablated in the sclera and/or cornea for collecting the percolating aqueous humor.

In one embodiment of the invention, the laser beam is optically combined with a visual system, using an optical combiner, to allow monitoring of the procedure. Optionally, the visual system is a ophthalmic microscope, for viewing the area of ablation by a physician performing the procedure. Alternatively or additionally, the visual system is an automatic vision system. Optionally, the optical combiner comprises a micro-manipulator, allowing the physician to change the laser aiming point and/or scan area. It is noted that standard micro-manipulators and beam combiners do not support an input from a spatially scanning laser beams.

An advantage of monitoring using a human or automatic visual system is that the ablation at a particular location on the eye can be stopped as soon as the aqueous humor starts percolating out, without requiring an optional self-limiting behavior of the a laser beam to take effect.

An aspect of some embodiments of the invention relates to using an automatic vision system for monitoring a non-penetrating filtration procedure. In one embodiment of the invention, the vision system detects percolation of liquid from the ablated sclera or cornea, thus identifying that ablation at the percolating point should be stopped. Optionally, this allows a greater degree of safety. Alternatively or additionally, the vision system controls the scanner (or laser) to reduce or eliminate the scanning of the laser at some points, while continuing the scanning at other points in the eye.

An aspect of some embodiments of the invention relates to an eye protector. In an exemplary embodiment, the eye protector prevents ablation by the laser outside of a pre-defined area, for example by physically blocking the laser light. Optionally, the eye protector is adhesive to the eye. Alternatively or additionally, the eye protector maintains open, during the procedure, one or more flaps formed in the eye. Alternatively or additionally, the eye protector is disposable.

There is thus provided in accordance with an exemplary embodiment of the invention, apparatus for ophthalmic surgery comprising:

a laser source that generates a laser beam;

a scanner comprising an input for said laser beam and an output of a spatially scanned laser beam;

controlling circuitry that drives said scanner to remove tissue in a desired pattern on the eye;

a microscope for viewing said tissue removal; and a beam combiner comprising a first input for a line of sight of said microscope and a second input for said spatially scanned beam. Optionally, the apparatus comprises a monitor for displaying a view of said tissue removal from said microscope. Alternatively or additionally, the apparatus comprises:

a camera which acquires an image of said tissue removal; and an image processor that processes said image.

In an exemplary embodiment of the invention, said circuitry uses said processing by said image processor to generate an indication of the tissue removal state. Preferably, said circuitry uses said indication to close a control loop of said tissue removal. Alternatively or additionally, said indication of tissue removal state comprises an indication of the thickness of remaining tissue in the area of tissue removal. Alternatively or additionally, said indication of tissue removal state comprises an indication of a percolation rate through the remaining tissue in the area of tissue removal.

In an exemplary embodiment of the invention, said apparatus comprises a frame attached to said combiner, which frame blocks laser from said laser. Alternatively or additionally, said laser source comprises a $CO_2$ laser source. Alternatively or additionally, said laser source comprises a UV laser source. Alternatively or additionally, said laser source generates a second, visible wavelength, aiming beam aligned with said laser beam. Alternatively or additionally, said laser beam is intense enough to remove sclera tissue by ablation.

There is also provided in accordance with an exemplary embodiment of the invention, apparatus for ophthalmic surgery comprising:

a laser source that generates a laser beam;

a scanner comprising an input for said laser beam and an output of a spatially scanned laser beam;

controlling circuitry that drives said scanner to remove tissue in a desired pattern on the eye;

a camera that acquires at least one image of said tissue removal; and an image processor that processes said acquired image to provide an input to said controlling circuitry. Preferably, said image processor generates an indication of a percolation rate in at least one location said eye. Alternatively or additionally, said image processor generates an indication of a remaining tissue thickness in at least one location said eye. Alternatively or additionally, said control circuitry varies a scanning path of said scanner, in response to said input. Alternatively or additionally, said control circuitry varies a beam intensity of said laser beam, as a function of the beam location, in response to said input. Alternatively or additionally, said control circuitry varies a spot size of said laser beam, as a function of the beam location, in response to said input. Alternatively or additionally, said control circuitry varies a pulse duration of said laser beam, as a function of the beam location, in response to said input. Alternatively or additionally, said control circuitry varies a scanning rate of said laser beam, as a function of the beam location, in response to said input.

There is also provided in accordance with an exemplary embodiment of the invention, an ophthalmic protector, comprising:

a flexible portion which is opaque to a laser light wave and transparent to at least some wavelengths of visible light and adapted for contact with an eye; and a transparent section, which is transparent to the laser light wave and sized for a non-penetrating filtration procedure. Preferably, said flexible portion is self-adhesive to said eye. Alternatively or additionally, said transparent section comprises an aperture in said flexible portion. Alternatively or additionally, said transparent section extends perpendicular to said flexible portion and towards said eye.

There is also provided in accordance with an exemplary embodiment of the invention, a method of performing a non-penetrating filtration procedure, comprising:

opening a flap in an eye, overlying a Schlemm's canal of said eye;

forming a percolation zone adjacent said Schlemm's canal by automatic scanning with a laser;

forming a reservoir in a sclera of said eye and in fluid connection with said percolation zone; and closing said flap. Preferably, forming a percolation zone comprises cleaning away charred tissue from said percolation zone. Alternatively or additionally, automatic scanning with a laser comprises automatically controlling at least one parameter of the scanning responsive to an effect of the laser on the tissue. Alternatively or additionally, said laser is a $CO_2$ laser.

BRIEF DESCRIPTION OF THE FIGURES

Exemplary, non-limiting embodiments of the invention will be described below, with reference to the following figures, in which the same elements are marked with the same reference numbers in different figures.

DETAILED DESCRIPTION OF SOME EMBODIMENTS

Figure 1:
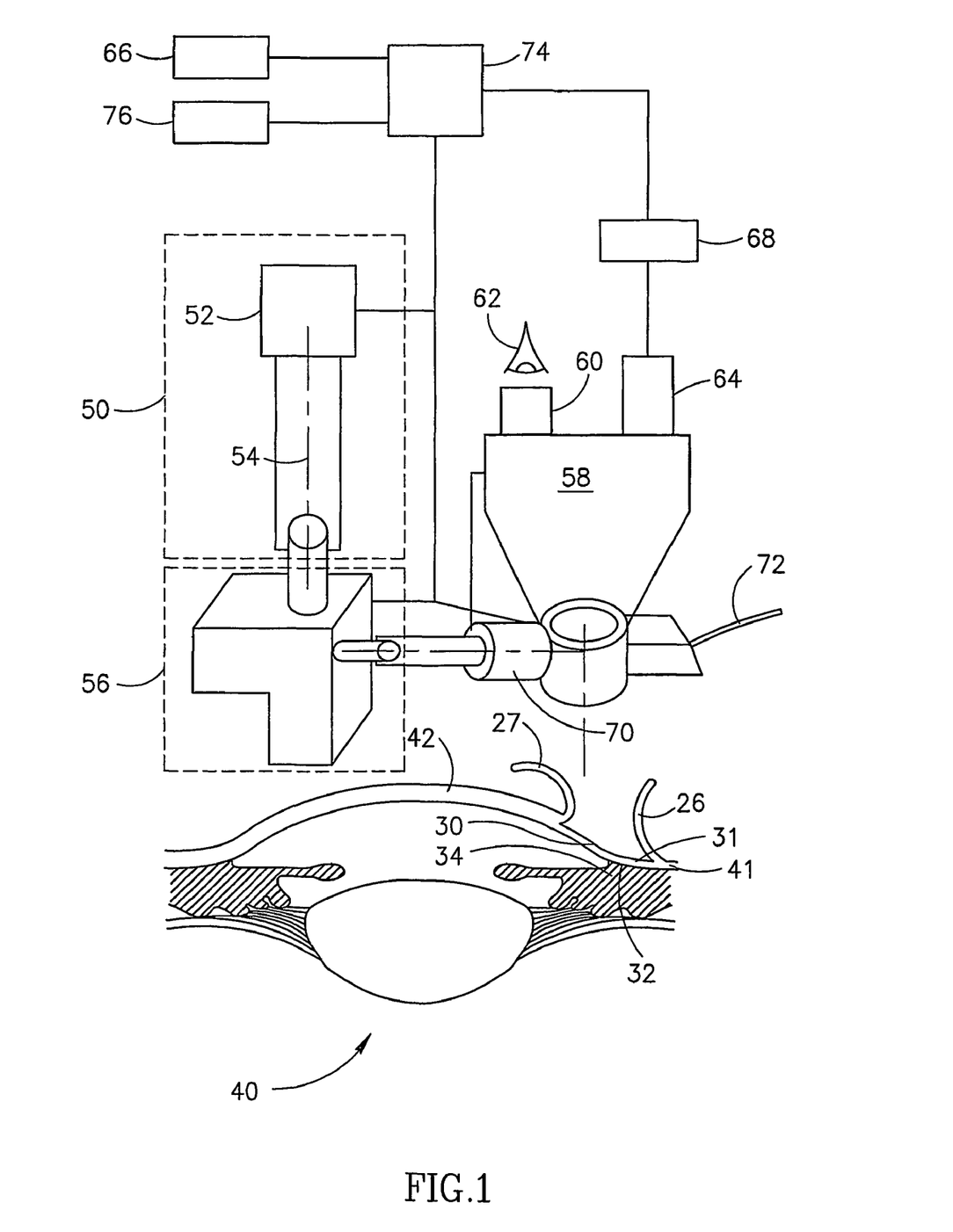
FIG. 1 is a schematic illustration of an exemplary ophthalmologic ablation system, during a non-penetrating filtration procedure in accordance with an exemplary embodiment of the invention.

FIG. 1 is a schematic illustration of an exemplary ophthalmologic ablation system 50, during a non-penetrating filtration procedure in accordance with an exemplary embodiment of the invention.

Referring first to an eye 40, an exemplary filtration procedure using system 50 comprises ablating parts of an area 31 of a sclera 41 and/or a cornea 42 in an area 30. Some of the ablation is directed to those areas overlying a Schlemm's canal 34 and/or trabecular meshwork 32. The size of area 30 is exaggerated in FIG. 1, as in many procedures, area 30 is significantly smaller than area 31 and may comprise substantially only the boundary area between cornea 42 and sclera 41 that overlies the Schlemm's canal. In some procedures, however, a larger portion of the cornea may be ablated. A more detailed description of an exemplary filtration procedure is provided below.

System 50 comprises a laser source 52 that generates an ablation laser beam 54. In one embodiment of the invention, a $CO_2$ laser is used, as the radiation from a $CO_2$ laser is well absorbed by water. Additional potential advantages of $CO_2$ lasers is their ability to prevent hemorrhage, low cost, small size and large power output. However, other lasers that are absorbed by water and/or the aqueous humor, such as ultraviolet lasers, may also be used. Further, other lasers, even those that are not absorbed by water may be used, however, this may reduce the general safety of the procedure. Alternatively to a laser, non-coherent light, such as produced by an infra-red flash lamp may be used.

The type of interaction of the laser (or other light) with the eye is typically that of ablation. However, other tissue removing interactions may be used as well, for example, vaporization and coagulation (and then optionally removal of the ablated tissue).

Optionally, source 52 also generates an aiming laser beam (not shown), having a low power and/or being visible. The aiming beam is optionally coaxial with ablation beam 54. This aiming beam may be formed by a separate laser boresighted with beam 54.

In one embodiment of the invention, laser beam 54 has a spot size smaller than the size of area 30 that is actually ablated. Beam 54 is optionally scanned over area 30 using a scanner 56, for example a mechanical, electro-optical or acusto-optical scanner. An exemplary scanner is described in greater detail below.

In some embodiments of the invention, the procedure is monitored through an ophthalmic microscope 58 or other suitable optical instrument. In one embodiment of the invention, a human viewer 62 views area 30 though an eyepiece 60 of microscope 58. Alternatively or additionally, the procedure is imaged using an imager 64, such as a CCD camera.

In an exemplary embodiment of the invention, beam 54 (and/or optional the optional aiming beam) is optically combined with the line of sight of microscope 58 and/or that of imager 64, using a beam combiner 70. Optionally, combiner 70 comprises a micro-manipulator, allowing the relative location of beams 54 and the line of sight of microscope 58 to be modified. Various types of micro-manipulators may be used, with a particular one being described below. In an exemplary embodiment, a joy stick 72 is provided on beam combiner 70 to control the relative lines of sight.

Unlike standard beam-combiners for ophthalmic use, combiner 70 is expected to receive a scanning beam, rather than a point source. Thus, the optics of combiner 70 are optionally designed to correctly aim the beam over a significant range of beam positions, such as ±2, ±4 or ±5 mm off center of the micro-manipulator input axis.

The image (or image sequence) acquired by imager 64 may be used in various ways. In one embodiment of the invention, the acquired image may be displayed, for example using a display 66. Alternatively or additionally, the acquired image is recorded. Alternatively or additionally, the acquired image is analyzed using an image processor 68. In some embodiments, the image and/or control parameters are transmitted to a remote location, such as using an Internet or other communication network.

In some embodiments of the invention, the image analysis is used to detect the percolation of aqueous humor. Alternatively or additionally, the image processing confirms that ablation beam 54 (or the aiming beam) are within a designated safety area. Alternatively or additionally, the image processing detects the depth of ablation, for example using stereoscopic images, by shadow analysis and/or by virtue of thin tissue being more transparent. The thickness of the tissue may be then determined, for example, by shining a strong light into the eye and measuring the relative or absolute amount of light exiting through the ablated tissue. Optionally, dye is provided into the eye, for example using ionophoresis and the degree of percolation is determined by viewing the color intensity of the percolating aqueous humor.

The detected percolation may be used to provide feedback to the treating physician, for example using display 66 or via an audio alarm (not shown). Alternatively or additionally, laser 52 may be shut off or beam 54 blocked, for example at scanner 56 or combiner 70. Alternatively or additionally, the image processing results may be used to complete a control loop, such as by controlling the scanning parameters of scanner 56.

In some cases, the laser beam may inadvertently penetrate into the eyeball. Optionally, such penetration is detected based on a flow rate of aqueous humor from the eye (which is a higher rate than that provided by percolation. Optionally, the procedure may be completed as a penetrating filtration procedure. Alternatively or additionally, a penetration is planned at at least one part of the eye. Optionally, the scanner is controlled to congeal and/or scar the tissue at or near the penetration area.

In one embodiment of the invention, a controller 74 is provided to receive the image processing results and apply suitable control to laser source 52, scanner 56, combiner 70. Alternatively or additionally, controller 74 is used for processing and displaying of data and/or for receiving input from the treating physician, such as procedure parameters. An suitable input device 76 may be provided.

Figure 2:
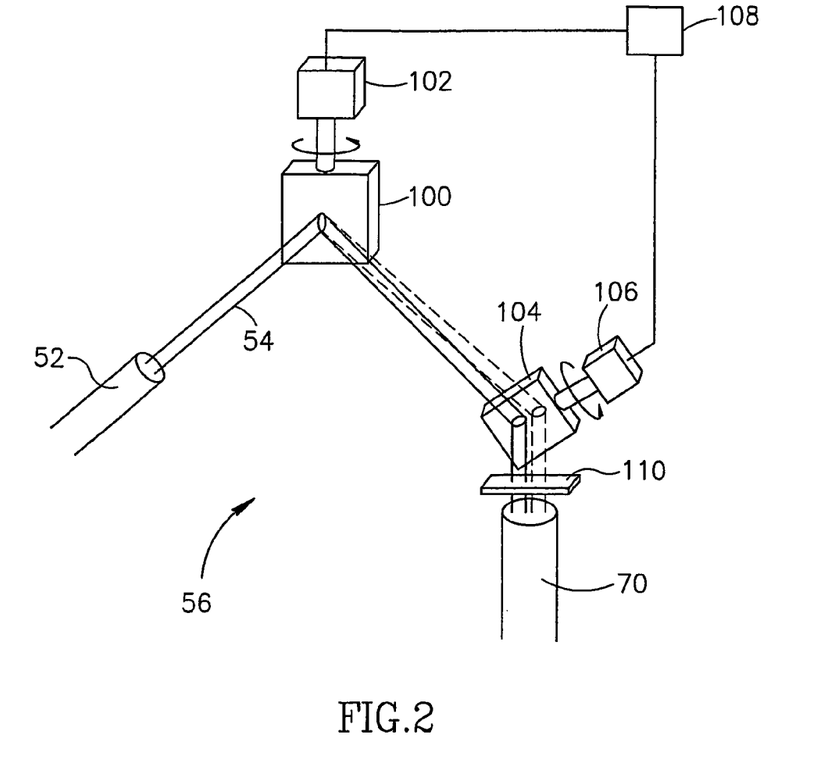
FIG. 2 is a schematic illustration of an exemplary scanner suitable for the system of FIG. 1.

FIG. 2 is a schematic illustration of an exemplary scanner 56 suitable for system 50. A beam 54 from laser source 52 is scanned in a first axis by a mirror 100, powered by a motor 102. A second mirror 104, powered by a second motor 106 scans the beam in another, optionally orthogonal axis. The two mirrors may be controlled by a scanning controller 108. The scanning is optionally continuous over a defined scanned area. In some embodiments, a same scanner may be used for scanning different sized and shaped areas. A beam attenuator 110 is optionally provided to selectively attenuate beam 54, for particular scanned locations in area 30 and 31 (FIG. 1). Attenuator 110 may be a one cell attenuator or it may be a spatial modulator. It should be noted that many different scanner designs can be used to generate a scanned beam, for example scanners using rotating prisms and acusto-optical scanners.

Additional potential advantages of a scanner which may be realized in some embodiments of the invention, include:

(a) limiting the laser and/or heat damage from nearby areas;

(b) providing depth control of the ablation in different parts of the eye;

(c) providing percolation rate control in different parts of the eye;

(d) when uniform ablation is desired, allowing selection of uniform depth or uniform tissue thickness; and/or (e) varying the scanning speed, intensity, pulse rate and/or other parameters based on the tissue type. Controller 74 may be used to simultaneously control laser 52 and scanner 56 to achieve various desired laser effects.

Figure 3:
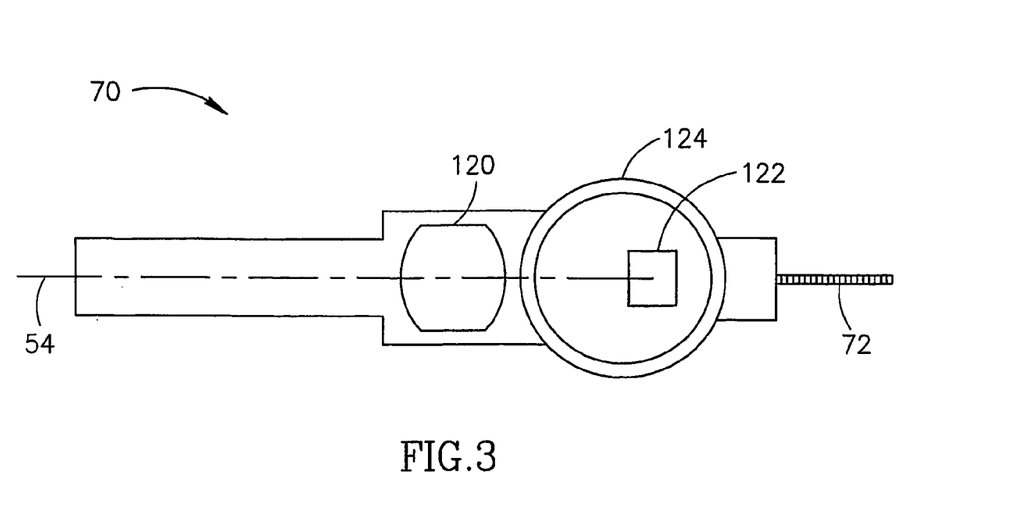
FIG. 3 is a schematic illustration of an exemplary micro manipulator for the system of FIG. 1, in accordance with an exemplary embodiment of the invention.

FIG. 3 is a schematic illustration of an exemplary combiner/micro-manipulator 70 for system 50, in accordance with one embodiment of the invention. As noted above, in some embodiments of the invention the input beam is scanned, rather than being restricted to a single spatial location. Thus, combiner 70 is optionally designed to properly combine the beam with the line of sight of microscope 58 over an expected range of off-axis positions of the scanning beam.

As shown in FIG. 3, a beam 54 enters combiner 70 and is optically processed by an optical system 120, which system controls the focusing of beam 54, so that it will be focused at areas 30 and 31, as required. In one embodiment of the invention, optical system 120 is configured and/or controlled so that beam 54 has the same focal plane as microscope 58. As will be described below, this can be achieved manually or automatically.

The optical path of microscope 58 may be delimited by an enclosing ring 124.

Beam 54 is combined with the optical path of microscope 58, using a beam combining element 122, for example a mirror that is transparent or semi-transparent to visible light and reflective for infra-red (or the wavelength of the laser). In an exemplary embodiment of the invention, a joy-stick 72 or other input means is provided for rotating beam combiner 122, so that the relative placement of laser beam 54 and the viewing field of microscope 58 can be controlled. Alternatively, the scanning area is defined and/or moved using scanner 56, which may require a larger and/or wider angle beam combiner to be provided. Alternatively or additionally, scanner 56 is provided as a single unit integral with combiner 70.

Figure 4:
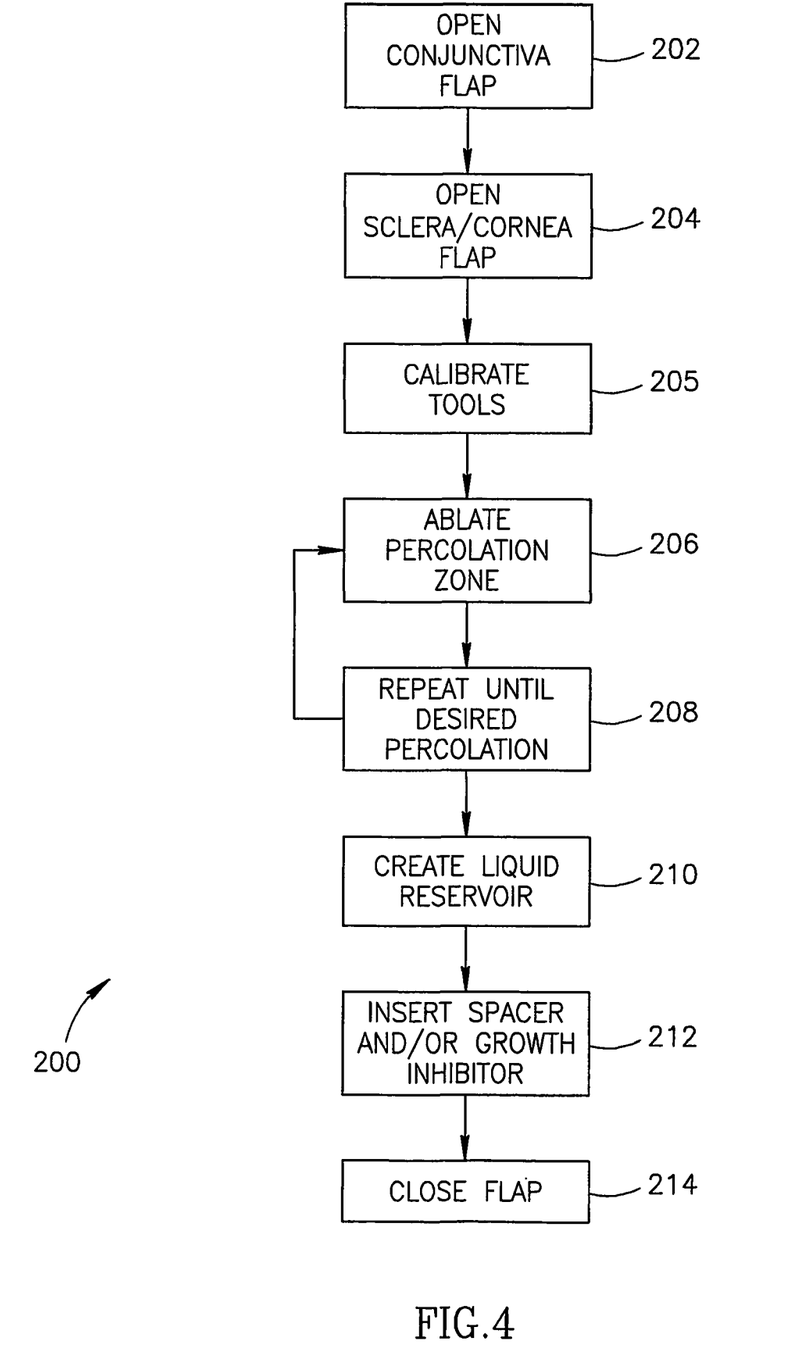
FIG. 4 is a flowchart of a method of non-penetrating filtration, in accordance with an exemplary embodiment of the invention.

FIG. 4 is a flowchart 200 of a method of non-penetrating filtration, in accordance with an exemplary embodiment of the invention. First, at 202, a flap 26 (FIG. 1) is formed in the conjunctiva of the eye. At 204, a flap is formed in the sclera 41 and cornea 42. Such flaps may be formed using any method known in the art, including using a scalpel, a laser and/or a dedicated cutting tool.

Figure 5:
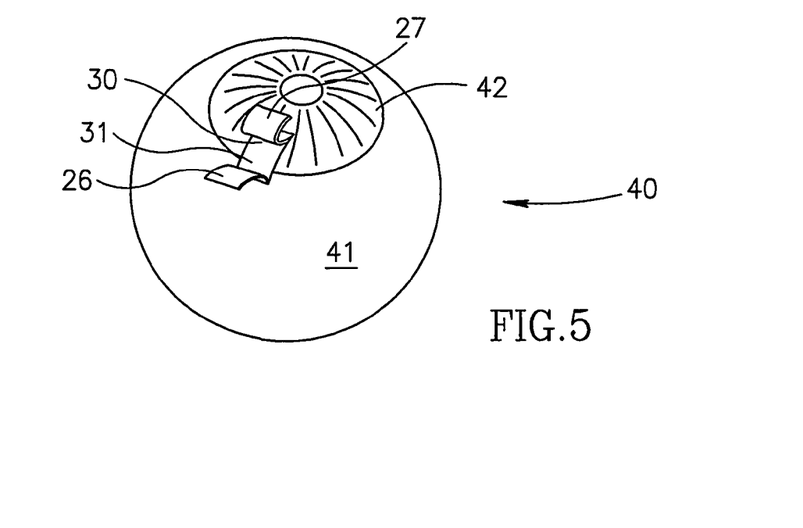
FIG. 5 is a perspective view of an eye showing an exposed ablation area, in accordance with an exemplary embodiment of the invention.

FIG. 5 is a perspective view of eye 40 showing an exposed ablation area 30 and 31, in accordance with an exemplary embodiment of the invention. In one embodiment of the invention, the flaps are opened so that they unroll in different directions. Thus, when the flaps are closed, the tip of one flap is under the base of the other flaps. This may provide a stronger seal. In the embodiment shown, the two flaps open in opposite directions, however, other angular relationships may be provided, for example an orthogonal relationship. Alternatively or additionally, the tip of scleral flap 27 is over sclera 41, for example, so that any swelling or inflammation will be less likely to affect the lens. Alternatively, the tip of flap 27 is over cornea 42 or, alternatively, over the boundary between the sclera and cornea.

At 205, the tools to be used are calibrated for the ablation area. In some embodiments, the tools are calibrated before the start of the procedure and/or periodically recalibrated during the procedure. Exemplary calibrations include: beam intensity, scanner/combiner alignment and/or laser focal plane. A laser focal plane calibration may be performed in conjunction with setting the microscope focal plane. Alternatively or additionally, a flexible focal distance combiner is used, which includes lens and/or other optical elements for varying the focal distance.

The target area may be shown, for example as a marking on mirror 122 (FIG. 3). Alternatively or additionally, a computer display may be provided showing an image of the eye and an estimated or imaged position of the laser beam. In some embodiments, a computer generated display showing, for example, scanning parameters, is combined with microscope 58, so viewer 62 can view the display via the microscope.

Depending on the particular implementation, microscope 58 and/or combiner 70 (which may be an integral unit with microscope 58), may or may not be in contact with eye 40 and/or ablated areas 30 and 31.

As will be described below, in an exemplary embodiment of the invention, both a percolation zone 220 (FIG. 6 below) for allowing percolation of the aqueous humor and a reservoir zone 222 (FIG. 6 below) for storing the up-welling humor until it is absorbed, may be formed. They may be formed with a same scanning setting, as part of a same scan, or separately. In other embodiments, only a percolation zone is formed. Typically, these zones are covered by a tissue flap when the procedure is completed.

At 206, a percolation zone 220 is ablated in area 30 overlying Schlemm canal 34 and trabecular meshwork 32. If the aqueous humor does not percolate (208) the ablation step is repeated. In one embodiment of the invention, once a percolation is detected or a minimal percolation rate is detected (both of which may be manually or automatically detected), the ablation is stopped. In another embodiment of the invention, ablation is stopped or slowed down at points where percolation is detected, but continued at other parts of area 30 and/or area 31. A minimal percolation zone may be defined, which is smaller than the actual ablated area of area 30. Thus, the ablation is closed circuit, i.e., iterative, or open circuit ablation can be practiced as well, at least for the reservoir, for example based on predefined laser beam settings.

Typically, the tissue in area 30 has a varying thickness, by ablating more at areas where there is less percolation, a uniformly thin filter area may be defined. Alternatively, a uniform (or other profile) percolation distribution can be achieved. Also, percolation-adapted ablation allows a matching of the scanning parameters to the tissue laser sensitivity. One or more of the following scanning parameters may be varied over the ablation area, to control the ablation:

(a) Spot size. A larger spot size provides a lower resolution and less energy per unit area. In some embodiments, non-circular spots are used, for example, elliptical, triangular, hexagonal and rectangular. Alternatively or additionally, a spot pattern may be provided. Such a pattern may be continuous, for example Gaussian or uniform, or discrete, for example, checkerboard. Exemplary circular spot sizes are between 0.1 mm and 1 mm, for example 0.8 mm.

(b) Dwell time. By varying the scanning speed, more energy can be deposited at locations that are not yet percolating and less energy at locations where no further ablation is desired. An exemplary dwell time is between 100 µs and 1000 ms, for example 400 µs.

(c) Beam intensity. This may be controlled, for example, by modulating the laser source or using attenuator 110, or another attenuator (uniform or spatially modulating) elsewhere along the optical path. The attenuators may selectively attenuate only the ablating beam (and not the optional aiming beam) for example having frequency selective properties or being having a suitable physical location. In some cases, the beam may be turned off for part of the scan. An exemplary source beam intensity is between 5 W and 15 W. The actual intensity that should be delivered to the eye can depend on various parameters, for example, the dwell time (and spot size), the age of the eye tissue, and the type of effect desired, e.g., ablation or coagulation.

(d) Beam location and scan pattern. In some embodiments, the beam scans the entire area, regardless of the effects of the beam. Alternatively, the beam may skip certain location and/or change the scan area definitions, on the fly, to match the percolating zones and/or required ablations.

(e) Scan path. In some embodiments, the scan path is selected so that there will be sufficient time to detect percolation at a location, between repeated ablations of the location. Alternatively or additionally, the scan path may be changed responsive to the initiation of percolation at some locations in the area. Optionally, the scan path overlaps itself, for example 10%. An exemplary scan path is by rows.

Optionally, the scanning is interleaved, with a greater separation between rows. The row direction may reverse itself every row.

(f) Scan shape. Various scan shapes may be used, to achieve variously shaped percolation and/or reservoir shapes.

(g) Laser pulse parameters, such as pulse length, pulse envelope and pulse repetition rate. In some embodiments, a pulsed laser is used. The laser may generate a pulsed beam or a continuous pulsed beam may be further temporally modulated. In one exemplary embodiment, a CW laser is used and modulated to have pulses between 1 µs and 1 ms and a repetition between 1 Hz and 1 kHz. Alternatively, a continuous beam is provided at the eye.

At 210, reservoir 222 (FIG. 6) is optionally created. Instead of using percolation to detect the reservoir depth, it may be estimated based on the laser energy deposition or it may be determined using image processor 68. In some embodiments, reservoir 222 is created while or prior to creating percolation zone 220.

Figure 6A:
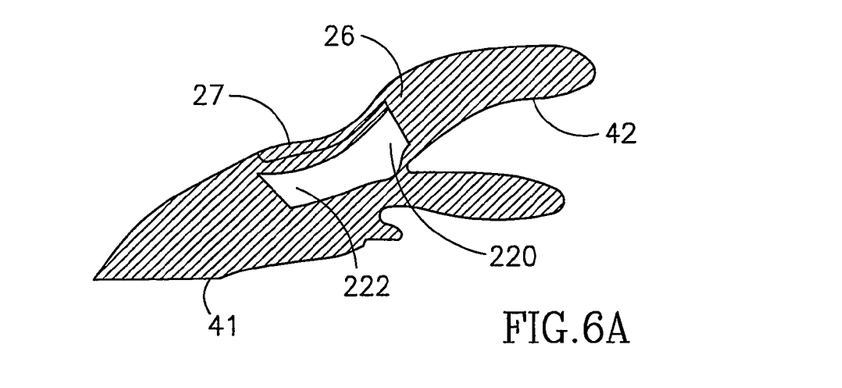
FIGS. 6A and 6B illustrate a completed percolation and reservoir system, from a side and a top view, in accordance with an exemplary embodiment of the invention.
Figure 6B:
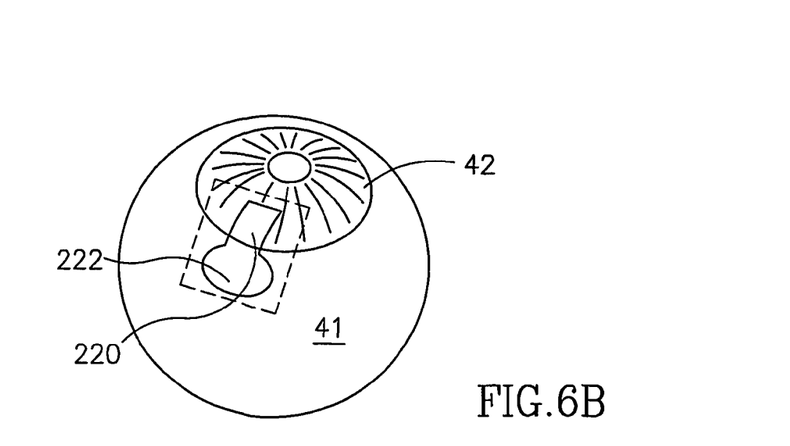

FIGS. 6A and 6B illustrate a completed percolation (220) and reservoir (222) system, from a side and a top view, in accordance with an exemplary embodiment of the invention.

FIG. 6A shows the situation after flaps 26 and 27 are closed. FIG. 6B is a top view, with the flaps shown as a dotted line.

As shown, reservoir 222 and percolation zone 220 have different geometries, which can include different shapes, sizes and/or depths. In an exemplary embodiment, percolation zone 220 is 3×3 mm and reservoir 222 is 5×3 mm. Alternative exemplary sizes for percolation zone 220 are between 2 and 5 mm by between 2 and 5 mm. Alternative exemplary sizes for reservoir 222 are between 3 and 5 mm by between 3 and 5 mm. The actual sizes of the zones may be fixed. Alternatively, one or both sizes decided ahead of time based on patient characteristics, for example, eye-size, age and intra-ocular pressure. Alternatively or additionally, the actual sizes may be decided during the procedure, for example, based on the percolation rate. Alternatively or additionally, the sizes of percolation zone 220 and/or reservoir 222 may be adjusted (up or down) in a later procedure.

However non-rectangular shapes can be provided, for example, round, elliptical or polygonal with, for example, between 3 and 10 facets. In particular, both convex and concave forms may be provided, for example to provide different perimeter-area ratios for reservoir 222 and/or percolation zone 220. Alternatively or additionally, at least part of one of the zones may be provided as a plurality of elongated zones.

Alternatively to contiguous reservoir and percolation zone, the two may be separated by one or more channels, for example a channel ablated in the sclera.

In some cases, ablation may cause charring of the eye or deposition of debris. Optionally, such charring is cleaned away using fluid or a wipe.

Optionally, prior to closing the flaps, a spacer is insert to maintain reservoir 222 and/or percolation zone 220 open (212), at least until the spacer is absorbed, as some spacers are formed of a bio-absorbable material. Exemplary spacers are:

(a) AquaFlow by Staar inc., formed of collagen;

(b) SK-Gel by Corneal Co., formed or reticulated hyaluronic acid;

(c) Hydrogel implants of various designs; and/or (d) Scleral implants formed of left over or harvested pieces of ocular tissue.

Alternatively or additionally to a spacer, an anti-metabolic material may be provided at the ablated area, to retard tissue ingrowth. Exemplary materials include: Mitomycin, typically contact-applied as a damp sponge for 2–3 minutes and 5-Fluoro-Uracil (5FU), typically applied as a series of sub-conjectival injection after the procedure.

At 214, the flaps are closed and sealed, for example using a laser, adhesive or by sewing.

Alternatively to scanning, in one embodiment of the invention, a large spot size is used, to cover the entire ablation area. Optionally, ablation will stop at portions of the ablated area that percolate, for example by a mechanism of the laser light being absorbed by the percolating aqueous humor only at the sufficiently ablated locations.

In another alternative to scanning, the procedure may be performed free-hand. Optionally, an integral scanner is provided in the probe. An aiming beam, which may be scanned or not, may be used to show the scan boundaries.

Figure 7:
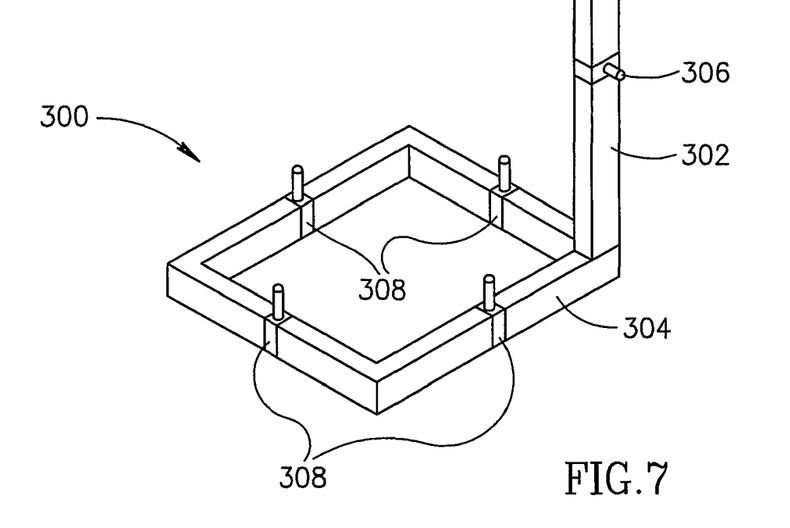
FIG. 7 illustrates an exemplary protective framework, in accordance with an embodiment of the invention.

FIG. 7 illustrates an exemplary protective framework 300, in accordance with an embodiment of the invention. Framework 300 is optionally attached to microscope 58 and blocks laser light from reaching outside of the ablation areas 30 and 31 and/or a safety zone defined around them. Alternatively or additionally, framework 300 may be attached to the patient. As shown, framework 300 comprises an attachment extension 302 for attaching the framework and a frame 304 defined, in this embodiment, by four bars. These bars may be wider than shown and/or may have a curtain attached to them for example a disposable adhesive (to the framework) curtain. The required focal distances of the procedure are optionally set using framework 300. A distance adjustment screw 306 may optionally be provided. Alternatively or additionally, framework geometry defining screws 308 may be provided, to control the shape and/or size of the framework and, thus, the ablateable zone. In some embodiments, frame 300 is not rectangular, for example being formed of a pliable wire. Alternatively or additionally, frame 300 may be semi-transparent, but not to except to beam 54. In one example, frame 700 comprises a holder, for example a clip, for a transparent plate the defines the laser action area.

Figure 8A:
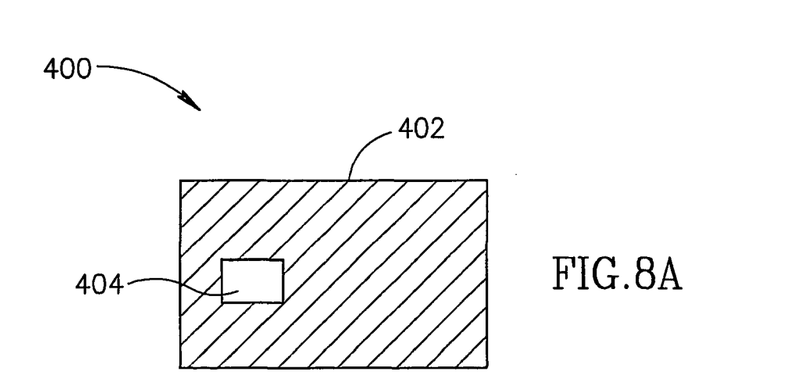
FIGS. 8A and 8B illustrate two alternative exemplary eye protectors in accordance with some embodiments of the invention.
Figure 8B:
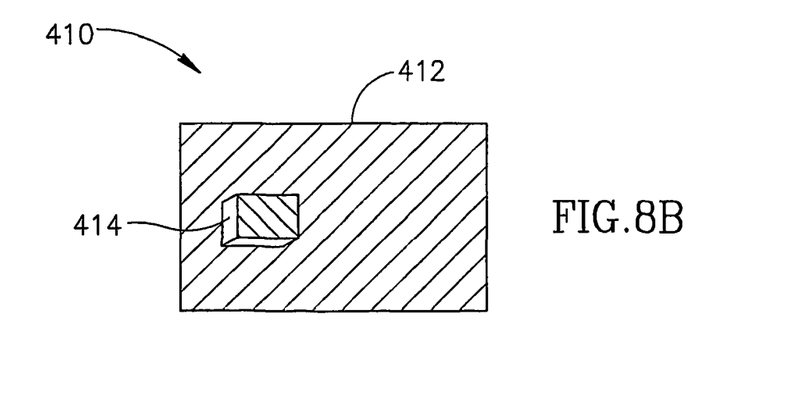

FIGS. 8A and 8B illustrate two alternative exemplary eye protectors in accordance with some embodiments of the invention.

FIG. 8A shows an aperture type protector 400, comprising a body 402 that blocks laser light and an aperture 404 which passes laser light. In one embodiment of the invention, body 402 is flexible and adhesive, for example being a silicon rubber sheet. Optionally, body 402, when attached to eye 40, maintains flaps 26 and 27 open. Alternatively to being flexible, body 402 may be rigid or plastically deformable. Alternatively to adhesive, other attachment methods, such as suturing, vacuum and/or self adhesion to the eye surface based on mechanical properties of the eye surface and/or body 402, may be used instead. Protector 400 may be disposable or sterilizable. Optionally, aperture 404 (or window 410, below) defines the shape of the ablation areas and/or shape of the flaps, for example if the flaps are cut using a laser.

FIG. 8B shows a window type protector 410 having a body 412 which can be the same as body 402. However, instead of an aperture 404, a window 414 may be provided for selective transmission of laser light. As shown, window 414 may protrude, for example towards the microscope, optionally to provide contact with the optical path and/or towards the eye, for example fitting into areas 30 and 31. Alternatively, a flat window may be provided. In an exemplary embodiment of the invention, window 414 is formed of a laser sensitive material, that turn opaque after a certain amount of energy is deposited in it, preventing inadvertent damage to the eye.

Alternatively, protector 410 may be attached to the microscope, for example using adhesive or being formed as a slide that can be coupled to the microscope. Alternatively to a slide, movable shutters are provided to limit the possible positions of the laser beam on the eye.

It will be appreciated that the above described methods of selective ablation of sclera and corneal tissue may be varied in many ways, including, changing the order of steps and the types of tools used. In addition, a multiplicity of various features, both of method and of devices have been described. In some embodiments mainly methods are described, however, also apparatus adapted for performing the methods are considered to be within the scope of the invention. It should be appreciated that different features may be combined in different ways. In particular, not all the features shown above in a particular embodiment are necessary in every similar embodiment of the invention. Further, combinations of the above features are also considered to be within the scope of some embodiments of the invention. Also within the scope of the invention are surgical kits which include sets of medical devices suitable for performing a single or a small number filtration procedures. When used in the following claims, the terms "comprises", "includes", "have" and their conjugates mean "including but not limited to".

It will be appreciated by a person skilled in the art that the present invention is not limited by what has thus far been described. Rather, the scope of the present invention is limited only by the following claims.

The invention claimed is:

1. Apparatus for ophthalmic surgery comprising:
a laser source that generates a laser beam;
a scanner comprising an input for said laser beam and an output of a spatially scanned laser beam; and
controlling circuitry configured to drive said laser beam over an eye in order to remove tissue, in a pattern suitable for achieving percolation for non-penetrating filtration of the eye, in which sufficient tissue is removed to allow percolation of fluid out of the eye and provide a reduction in an elevated intra-ocular pressure, without penetrating into the eye.

2. Apparatus according to claim 1, comprising:
a camera which acquires an image of said tissue removal; and
an image processor that processes said image.

3. Apparatus according to claim 2, wherein said circuitry uses said processing by said image processor to generate an indication of the tissue removal state.

4. Apparatus according to claim 3, wherein said circuitry uses said indication to close a control loop of said tissue removal.

5. Apparatus according to claim 3, wherein said indication of tissue removal state comprises an indication of the thickness of remaining tissue in the area of tissue removal.

6. Apparatus according to claim 3, wherein said indication of tissue removal state comprises an indication of a percolation rate through the remaining tissue in the area of tissue removal.

7. Apparatus according to claim 1, comprising a frame adapted to block the laser beam from impinging on an area of said eye.

8. Apparatus according to claim 1, wherein said laser source comprises a $CO_2$ laser source.

9. Apparatus according to claim 1, wherein said laser source comprises a UV laser source.

10. Apparatus according, to claim 1, comprising an additional laser source adapted to generate a second, visible wavelength, aiming beam aligned with said laser beam.

11. Apparatus according to claim 1, wherein said laser beam is intense enough to remove sclera tissue by ablation.

12. Apparatus according to claim 1, comprising:
a microscope for viewing said tissue removal.

13. Apparatus according to claim 12, comprising a monitor for displaying a view of said tissue removal from said microscope.

14. Apparatus according to claim 12, comprising:
a beam combiner comprising a first input for a line of sight of said microscope and a second input for said spatially scanned beam.

15. Apparatus according to claim 1, wherein the controlling circuitry is adapted to drive the scanner over an area greater than 9 square millimeters.

16. Apparatus according to claim 1, wherein the controlling circuitry is adapted to drive the scanner in a pattern determined responsive to feedback on percolation formation in a scanned area.

17. Apparatus for ophthalmic surgery comprising:
a laser source that generates a laser beam;
a scanner comprising an input for said laser beam and an output of a spatially scanned laser beam;
controlling circuitry that drives said scanner to remove tissue in a desired pattern on the eye;
a camera that acquires at least one image of said tissue removal; and
an image processor that processes said acquired image to provide an indication of a percolation rate in at least one location on the eye, as an input to said controlling circuitry.

18. Apparatus according to claim 17, wherein said image processor generates an indication of a remaining tissue thickness in at least one location on said eye.

19. Apparatus according to claim 17, wherein said control circuitry varies a scanning path of said scanner, in response to said input.

20. Apparatus according to claim 17, wherein said control circuitry varies a beam intensity of said laser beam, as a function of the beam location, in response to said input.

21. Apparatus according to claim 17, wherein said control circuitry varies a spot size of said laser beam, as a function of the beam location, in response to said input.

22. Apparatus according to claim 17, wherein said control circuitry varies a pulse duration of said laser beam, as a function of the beam location, in response to said input.

23. Apparatus according to claim 17, wherein said control circuitry varies a scanning rate of said laser beam, as a function of the beam location, in response to said input.

24. A method of treating an eye, comprising:
providing a laser scanner for eye treatment, including:
a laser source that generates a laser beam;
a scanner comprising an input for said laser beam and an output of a spatially scanned laser beam; and
controlling circuitry configurable to drive the scanner to direct the laser beam in a desired pattern;
identifying an area of the eye overlying at least one of a Schlemm canal and a trabecular meshwork; and
driving the laser scanner to ablate tissue in the identified area until percolation is achieved in at least a portion of the area, in a manner suitable for reducing an elevated intra-ocular pressure, without penetrating into the eye.

25. A method according to claim 24, comprising (a) forming a flap in the identified area; and (b) after said driving inserting a spacer between said flat and said eye.

26. A method according to claim 24, wherein identifying the area comprises identifying an area at least partially in sclera tissue of the eye.

27. A method according to claim 24, wherein the laser source comprises a $CO_2$ laser source.

28. A method according to claim 24, comprising collecting feedback on progression of the ablation and wherein driving the laser scanner comprises driving responsive to the collected feedback.

* * * * *

UNITED STATES PATENT AND TRADEMARK OFFICE
CERTIFICATE OF CORRECTION

| | |
|---|---|
| PATENT NO. | : 7,135,016 B1 |
| APPLICATION NO. | : 10/240505 |
| DATED | : November 14, 2006 |
| INVENTOR(S) | : Ehud Assia et al. |

It is certified that error appears in the above-identified patent and that said Letters Patent is hereby corrected as shown below:

On the title page,

Item (75)    Inventors: should read as follows:

-- Ehud Assia, Tel-Aviv (IL); --

Signed and Sealed this

Seventh Day of October, 2008

JON W. DUDAS
*Director of the United States Patent and Trademark Office*